United States Patent
Kuiper et al.

(10) Patent No.: US 7,808,717 B2
(45) Date of Patent: Oct. 5, 2010

(54) APPARATUS FOR FORMING VARIABLE FLUID MENISCUS CONFIGURATIONS

(75) Inventors: Stein Kuiper, Eindhoven (NL); Gerjan Franciscus Arthur Van De Walle, Eindhoven (NL); Edwin Maria Wolterink, Eindhoven (NL); Mark Jozef Willem Mertens, Eindhoven (NL); Bokke Johannes Feenstra, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1416 days.

(21) Appl. No.: 10/536,922

(22) PCT Filed: Nov. 21, 2003

(86) PCT No.: PCT/IB03/05325

§ 371 (c)(1),
(2), (4) Date: May 31, 2005

(87) PCT Pub. No.: WO2004/051323

PCT Pub. Date: Jun. 17, 2004

(65) Prior Publication Data

US 2006/0079728 A1    Apr. 13, 2006

(30) Foreign Application Priority Data

Dec. 3, 2002   (EP) ................. 020800603
Feb. 4, 2003   (EP) ................. 031002298

(51) Int. Cl.
  *G02B 1/06*   (2006.01)
  *G02B 3/12*   (2006.01)
(52) U.S. Cl. ............... 359/665; 359/666; 359/667
(58) Field of Classification Search .......... 359/665–667
See application file for complete search history.

(56) References Cited

U.S. PATENT DOCUMENTS

| 2007/0115789 | A1* | 5/2007 | Liedenbaum | 369/103 |
| 2008/0247051 | A1* | 10/2008 | Hendriks et al. | 359/666 |
| 2008/0265037 | A1* | 10/2008 | T'Hooft et al. | 235/470 |
| 2009/0002807 | A1* | 1/2009 | Hendriks et al. | 359/319 |

FOREIGN PATENT DOCUMENTS

WO   WO9918456 A1   4/1999
WO   WO0058763 A1   10/2000

* cited by examiner

*Primary Examiner*—Evelyn A. Lester

(57) ABSTRACT

Apparatus for providing a fluid meniscus with variable configurations by means of electrowetting. A fluid chamber (5) holds two different fluids (A, B) separated by a meniscus (14) of which the edge, having different sides, is constrained by the fluid chamber. A first electrowetting electrode (2a) is arranged to act on a first side of the meniscus edge and a second electrowetting electrode (2a') is arranged to act separately on a second side of the meniscus edge. Selected meniscus configurations can be formed by providing selected voltages to the first and second electrowetting electrodes respectively.

22 Claims, 5 Drawing Sheets

APPARATUS FOR FORMING VARIABLE FLUID MENISCUS CONFIGURATIONS

The present invention relates to apparatus for forming variable fluid meniscus configurations.

A variable meniscus is described in International patent publication WO 99/18456. In this arrangement, the lens comprises a chamber filled with a conductive liquid, a droplet of an insulating, non-miscible liquid being held in a surface zone of the chamber wall. The droplet is positioned in the zone by means of a combination of a hydrophobic layer and an adjacent hydrophilic layer. Application of a voltage to electrodes in the chamber causes the lensing upper surface of the droplet to become more convex. In one embodiment, the hydrophobic and hydrophilic layers are arranged along a cylindrical surface, the sides of the droplet being positioned axially along the cylindrical surface, and thereby centered, by the hydrophilic layer when no voltage is applied and by a series of axially-spaced electrodes along the sides of the cylinder when a voltage is applied.

A further variable meniscus having such an arrangement is described in International patent publication WO 00/58763. The proposed means for centering a droplet of insulating liquid is a bell-mouthed recess formed of an insulating layer in an adjustable lens. The sides of the recess are arranged so as to keep the droplet centered within the recess and to provide a convex lensing surface on the droplet. Since the base of the recess is formed of the same material as the sides of the recess, such material must be chosen to be transparent if the lens is to be operative.

It is an object of the present invention to provide improvements to variable menisci such as the prior art arrangements described above.

In accordance with one aspect of the present invention, there is provided apparatus for providing a fluid meniscus with variable configurations by means of electrowetting, the apparatus comprising:

a fluid chamber;

two different fluids separated by a meniscus of which an edge, having different sides, is constrained by the fluid chamber;

a first electrowetting electrode and a second electrowetting electrode, the first electrowetting electrode being arranged to act on a first side of the meniscus edge and the second electrowetting electrode arranged to act separately on a second side of the meniscus edge; and a voltage control system for providing a different voltage to said first and second electrowetting electrodes respectively to form a selected meniscus configuration.

The apparatus of this aspect of the present invention, when used as an optical device, provides for the formation of desirable fluid meniscus configurations which are not rotationally symmetric about the optical axis of the device. For example, configurations which are tilted and/or astigmatic about the optical axis may be provided. A range of fluid meniscus configurations can be formed in a variable, controllable manner. Exemplary meniscus configurations include flat shapes and anamorphic lens shapes capable of the precise refractive or reflective angular deflection of light in up to three dimensions. The meniscus configurations can be formed accurately and efficiently under the application of variable voltage patterns applied across the configuration of electrodes and a common electrode. Other types of meniscus lens configurations, for example approximately spherical lens shapes and more complex lens shapes may also be formed using the same apparatus, and different types of voltage patterns.

In accordance with a further aspect of the invention, there is provided apparatus comprising an image sensor for the recording of an image scene, a variable fluid meniscus and a controller adapted to alter the shape of the meniscus to provide at least:

a first configuration of the variable fluid meniscus, said first configuration directing a first region of the image scene to be recorded towards said sensor; and a second configuration of the variable fluid meniscus, said second configuration directing a second, different, region of the image scene to be recorded towards said sensor.

The apparatus of this aspect of the invention allows high resolution digital images of a target image scene to be recorded without the need for a high resolution sensor. Current image recording methods include the use of expensive and complex imaging sensors. This aspect of the present invention provides new means for the efficient and simple recording of a high resolution digital image of a target image scene using variable fluid meniscus apparatus.

Additionally, this image scene recording technique provides advantages over known superresolution methods for digital imaging. These include the possibility for effective image improvement algorithms to be applied only once to the recorded image scene, the individual image regions being seamed together. Also, as the individual image regions are well imaged, and the applied seaming technique to obtain the overall recorded image can be a relatively simple image processing step.

According to a further aspect of the invention there is provided apparatus for providing fluid menisci with variable configurations by means of electrowetting, the apparatus comprising:

a set of fluids forming a first fluid meniscus and a second fluid meniscus between respective different fluids, each fluid meniscus having a variable configuration;

a set of electrodes arranged to act on the set of fluids by electrowetting to vary the configurations of the first and second fluid menisci; and a voltage control system for providing selected voltages to said set of electrodes to form said first and second fluid menisci into selected configurations.

By forming the two different menisci into selected configurations, the apparatus can be used to modify the wavefront of a radiation beam in two steps, a first such modification being provided by passage of the radiation beam across the first meniscus and a second such modification being provided by passage of the radiation beam across the second meniscus. In one embodiment, the set of fluids is contained in a single fluid chamber; in this embodiment one of the fluids preferably forms a central common fluid component located between the first and second menisci. In another embodiment, the set of fluids is arranged two fluid chambers, each containing one of the first and second menisci. In one embodiment the electrodes are arranged such that the configurations of the first and second menisci are independently controllable; in a further embodiment the electrodes are arranged such that the configurations of the first and second menisci are controllable in dependence on each other.

According to a further aspect of the invention there is provided medical imaging apparatus including a capsule for use in vivo, said capsule comprising an image sensor (34) for the recording of an in vivo image scene and a variable fluid meniscus arrangement (32).

The variable fluid meniscus arrangement may be a lens and/or a deflector. For the operation of the arrangement as a deflector, the medical imaging apparatus is preferably provided with a controller adapted to alter the shape of the variable fluid meniscus of the arrangement to provide at least:

a first configuration of the variable fluid meniscus for imaging a first in vivo image scene onto said image sensor; and a second configuration of the variable fluid meniscus for imaging a different, second in vivo image scene on said image sensor.

In this arrangement, the capsule can be provided with a continuously variable focus and/or variable directional imaging function in a compact, low power consumption and lightweight module.

Features and advantages of the invention will become apparent from the following description of preferred embodiments of the invention, given by way of example only and made with reference to the accompanying drawings.

Figure 1:
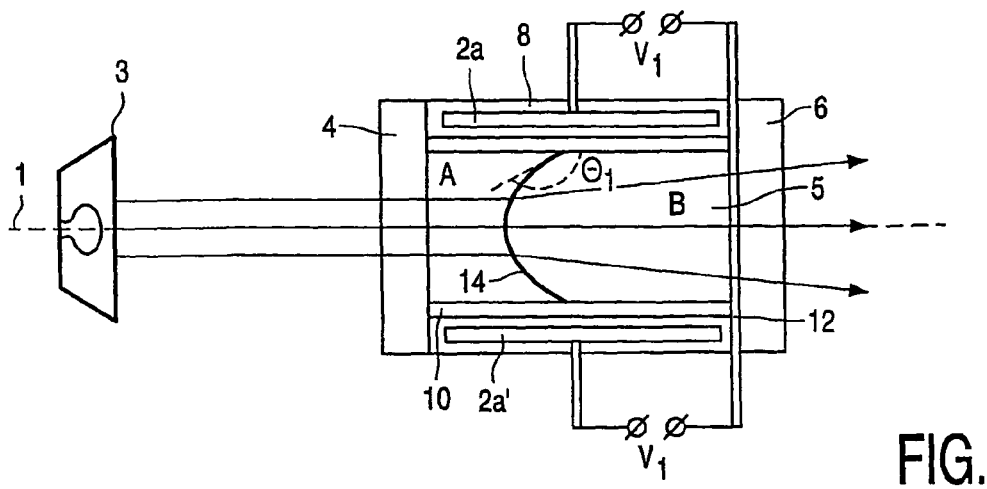
FIGS. 1 to 3 show a simplified side view cross-section of variable anamorphic lens shape apparatus in various focusing stages in accordance with an embodiment of the present invention.
Figure 2:
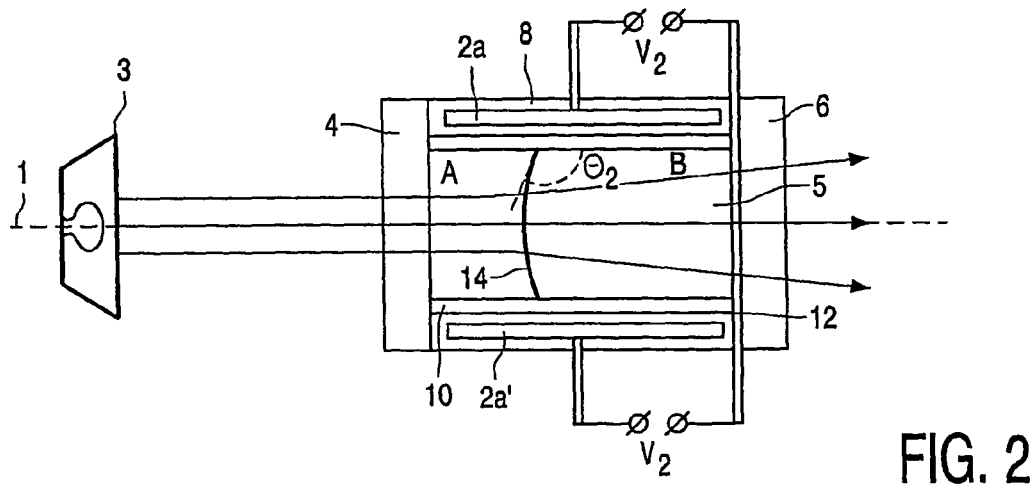
Figure 3:
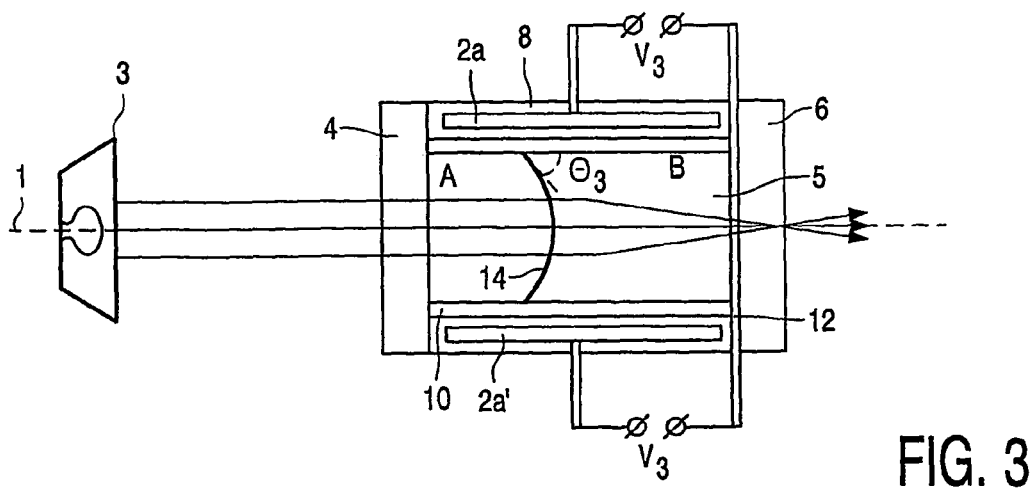

FIGS. 1 to 3 are schematic side view cross-sections which show apparatus for forming variable anamorphic meniscus lens shapes according to an embodiment of the present invention. The apparatus in this embodiment is a variable focus anamorphic meniscus lens comprising a cylindrical arrangement of a plurality of electrowetting electrodes, referred to as sidewall segment electrodes arranged side by side and spaced about the optical axis 1 of a beam of light provided by a suitable light source 3, for example a semiconductor laser, although it should be noted that, in all of the following embodiments, the light source may be replaced by for example an image scene if the apparatus is used for example in a camera. A description of the structure and function of the lens follows.

Figure 4:
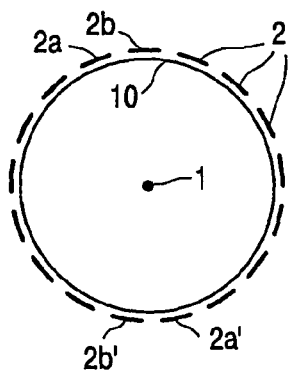
FIG. 4 shows a top view cross-section of an electrode configuration for use in the variable anamorphic lens shape apparatus in accordance with an embodiment of the present invention.

FIG. 4 shows a cross-section, taken perpendicular to the optical axis 1, of a configuration of a plurality of segment electrodes about the optical axis 1 of the lens in this embodiment. The sidewall segment electrodes are grouped in pairs illustrated by example with labels 2a and 2a', 2b and 2b', etc.

Each member of a pair lies parallel to the other on the opposite side of the optical axis 1. A voltage control circuit (not shown) is connected to the electrode configuration to apply varying voltage patterns to the segment electrodes 2.

The arrangement of segment electrodes 2, along with a fluid contact layer 10, form a tube sealed by means of a front element 4 and a back element 6 to form a fluid chamber 5 containing two fluids. In this example, the front and back elements, 4 and 6 respectively, are transparent.

In this embodiment the two fluids consist of two non-miscible liquids in the form of a non-conducting non-polar first liquid A, such as a silicone oil or an alkane, and an electrically conducting polar second liquid B, such as an aqueous salt solution. The two liquids are preferably arranged to have an equal density, so that the lens functions independently of orientation, i.e. without dependence on gravitational effects between the two liquids. This may be achieved by appropriate selection of the first and second liquid constituents.

Depending on the choice of the oil used for liquid A, the refractive index of the oil may vary between 1.25 and 2.00. Likewise, when liquid B is an aqueous salt solution the refractive index may vary between 1.33 and 1.60 depending on the amount of salt added. It should be noted that a higher refractive index can be achieved using alternative conductive liquids, e.g. ethylene glycol. The fluids in this embodiment are selected such that the first liquid A has a higher refractive index than the second liquid B.

The sidewall segment electrodes are formed from a conductive material, for example metal, and coated by an insulating layer 8, formed for example of parylene. Each individual segment electrode is also insulated with respect to the adjacent electrodes. The cylindrical inner surface described by the arrangement of segment electrodes is coated with a continuous, uniform thickness, fluid contact layer 10, which reduces the hysteresis in the contact angle of the meniscus with the cylindrical wall of the fluid chamber. The fluid contact layer is preferably formed from an amorphous fluorocarbon such as insulating Teflon™ AF1600 produced by DuPont™. The wettability of the fluid contact layer by the second fluid is substantially equal on both sides of the intersection of the meniscus 14 with the fluid contact layer 10 when no voltage is applied. Alternatively, the insulating layer and the fluid contact layer may simply comprise a single continuous and uniform thickness layer of Teflon AF1600.

A common endwall electrode 12, in this example of an annular shape, is arranged at one end of the fluid chamber, in this case, adjacent the back element. The endwall electrode 12 is arranged with at least one part in the fluid chamber such that the electrode acts on the second fluid B.

The two liquids A and B in this embodiment are non-miscible liquids so as to tend to separate into two fluid bodies separated by a meniscus 14. The meniscus 14 has one continuous edge lying in contact with the fluid contact layer 10. When no voltage is applied between the sidewall and endwall electrodes, the fluid contact layer has a higher wettability with respect to the first liquid A than the second liquid B. Due to electrowetting, the wettability by the second liquid B varies under the application of a voltage between a sidewall segment electrode 2 and the endwall electrode 12, which tends to change the contact angle of the meniscus at its edge (the line of contact between the fluid contact layer 10 and the two liquids A and B). The shape of the meniscus is thus variable in dependence on the applied voltage at each segment electrode 2.

FIGS. 1 to 3 are illustrations of the case where the sidewall segment electrodes 2 are driven in parallel with the same applied voltages, such that the meniscus adopts various different rotationally symmetric approximately spherical lens shapes. Later, it will be described how the application of different voltage levels to the different electrodes in controlled patterns is used to generate variable anamorphic lens shapes.

Referring now to FIG. 1, when a low voltage $V_1$, e.g. between 0 V and 20 V, is applied between the sidewall segment electrodes 2 and the endwall electrode, the meniscus adopts a first concave meniscus shape. In this configuration, the initial contact angle $\theta_1$ between the meniscus and the fluid contact layer 10, measured in the liquid B, is for example approximately 140°. Due to the higher refractive index of the first liquid A than the second liquid B, the lens formed by the meniscus, here called meniscus lens, has a relatively high negative power in this configuration.

To reduce the concavity of the meniscus shape, a higher magnitude of voltage is applied between the sidewall segment electrodes 2 and the endwall electrode 12. Referring now to FIG. 2, when an intermediate voltage $V_2$, e.g. between 20 V and 150 V, depending on the thickness of the insulating layer, is applied between the electrodes the meniscus adopts a second concave meniscus shape having a radius of curvature increased in comparison with the meniscus in FIG. 1. In this configuration, the intermediate contact angle $\theta_2$ between the first liquid A and the fluid contact layer 10 is for example approximately 100°. Due to the higher refractive index of the first liquid A than the second liquid B, the meniscus lens in this configuration has a relatively low negative power.

To produce a convex meniscus shape, a yet higher magnitude of voltage is applied between the sidewall segment electrodes 2 and the endwall electrode 12. Referring now to FIG. 3, when a relatively high voltage $V_3$, e.g. 150 V to 200 V, is applied between the electrodes the meniscus adopts a meniscus shape in which the meniscus is convex. In this configuration, the maximum contact angle $\theta_3$ between the first liquid A and the fluid contact layer 10 is for example approximately 60°. Due to the higher refractive index of the first fluid A than the second fluid B, the meniscus lens in this configuration has a positive power.

Thus, through variation of the applied voltage, various different approximately spherical meniscus lens shapes can be generated in the plane of one sidewall segment electrode pair.

An anamorphic lens generally focuses incoming light rays at two focal lines which are generally orthogonal and axially separated. The anamorphic lens exhibits a different value of focal power or magnification in two generally orthogonal axes, one of which is referred to as the cylindrical axis, arranged in a plane perpendicular to the optical axis. These focal properties characterize the optical condition 'astigmatism'. Anamorphic lens shapes include those of an approximately cylindrical and approximately spherocylindrical nature.

By applying individual and different voltages across each sidewall segment electrode pair 2a and 2a', 2b and 2b', etc. and the endwall electrode 12, anamorphic meniscus lens shapes can be formed of variable focal powers and/or variable amounts and types of astigmatism. The applied voltages vary gradually between sidewall segment electrodes in the direction of the meniscus lens circumference. The average applied voltage is related to the focal power whilst the largest voltage variation is related to the cylindrical value.

Figure 7:
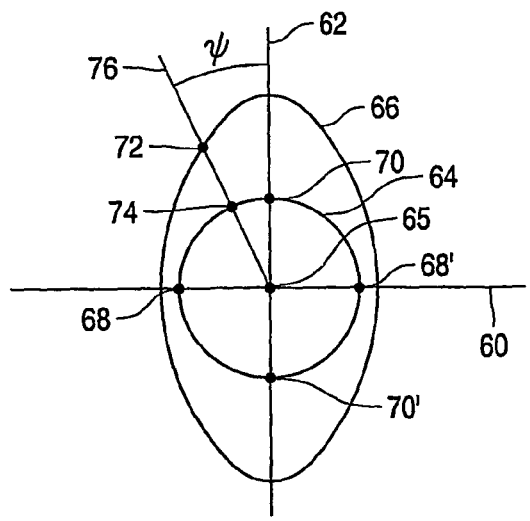
FIG. 7 shows a graphical representation of applied voltage across an electrode configuration according to an embodiment of the invention.

FIG. 7 shows a graphical representation of relative values of voltages in patterns of voltages applied to produce anamorphic lens shapes. Any relative value of voltage applied at an electrode can be determined by taking the radial distance between the two lines 64, 66 at the appropriate angular position corresponding to the angular location of the center of the electrode about the optical axis 65. In the following, the angular positions corresponds the position about the circumference of the arrangement of segment electrodes described using FIG. 5a. The graphical representation shows a plot on perpendicular axes of this variation of voltages corresponding to a cross-sectional view perpendicular to an optical axis of the fluid meniscus lens. The graphical representation shows a first axis 60 and a second axis 62, arranged perpendicular to each other. The first axis 60 corresponds to a cylindrical axis of the meniscus shape. The circular circumferential line 64 is used to represent all the possible locations of the centers of the segment electrodes 30 (not shown in FIG. 7) about the optical axis. Locations corresponding to the centers of two pairs of the rectangular segment electrodes, perpendicular to each other, are shown; 68 and 70 respectively, in this case lying along axes 60 and 62 respectively.

Applied voltage line 66 shows relatively the applied value of voltage corresponding to a point on the circumferential line 64 of the electrode arrangement. In the representation, the radial distance between a point on the applied voltage line 66 and the corresponding point on the circumferential line 64 represents the relative applied voltage, the common radial line lying at a specific angle from one of either axis 60 or 62. By way of example, this is illustrated in FIG. 7 wherein label 72 shows the point on the applied voltage line 66 and label 74 shows the corresponding point on the circumferential line 64. Both of these points lie along the common radial line 76 at angle $\theta$ from, in this case, axis 62.

Figure 6:
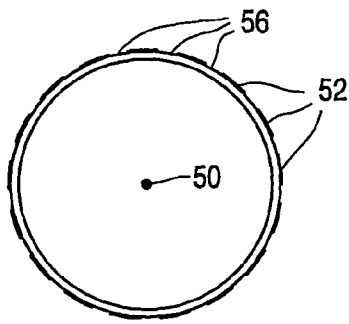
FIG. 6 shows a further alternative electrode configuration for use in a variable anamorphic lens shape apparatus according to an embodiment of the invention.

The greater the radial distance between the point on the applied voltage line 66 and the corresponding point on the circumferential line 64, the greater the relative applied voltage. For example, as FIG. 6 shows, a relatively high voltage is applied across segment electrode pair represented by locations 70, whereas a relatively low voltage is applied across segment electrode pair represented by locations 68. The voltages applied across each respective intermediate segment electrode 30, arranged between a member of the segment electrode pair represented by locations 70 and a member of the segment electrode pair represented by locations 68, decreases gradually.

Electronic rotation by appropriate means, for example a manually operated applied voltage controller, of the pattern of applied voltages between the pairs of sidewall segment electrodes and the endwall electrode enables the correct angular position of the cylindrical axis of the anamorphic lens to be obtained.

In this embodiment the width of each segment electrode is less than half, preferably less than one eighth, of the internal diameter of the cylindrical arrangement of electrodes. This involves the use of sufficient segment electrodes, preferably sixteen or above, to reduce observation at the center of the meniscus lens of significant effects caused by discrete steps of meniscus contact angle between the cylindrical walls of the fluid chamber.

Figure 5:
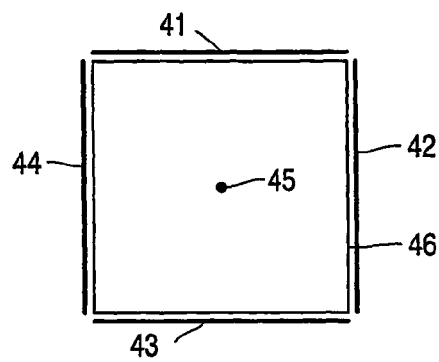
FIG. 5 shows an alternative electrode configuration for use in the variable anamorphic lens shape apparatus according to an embodiment of the invention.

FIG. 5, being a top view cross-section taken perpendicular to the optical axis of the lens, shows an alternative electrowetting electrode configuration for producing anamorphic meniscus lens shapes. Four rectangular segment electrodes 41, 42, 43, 44 are spaced about the optical axis 45 of the lens in a square formation with their longitudinal edges parallel, thus forming a square enclosure. In this embodiment opposite segment electrodes 41 and 43 are arranged as a pair and 42 and 44 as a pair. The inner surface of the segment electrodes is covered with a continuous, uniform thickness, electrically insulating, fluid contact layer 46, formed for example of Teflon™ AF1600, which constrains the meniscus edge.

Referring now to both FIGS. 1, 4 and 5 and with substitution of the configuration of segment electrodes shown in FIG. 4 by the alternative construction of four segment electrodes, a voltage pattern can be applied between the sidewall segment electrodes and an endwall electrode similar to the annular electrode 12 in the first embodiment. Through combination of different applied voltages for the segment electrode pairs, an anamorphic meniscus lens shape which is approximately cylindrical or spherocylindrical can be achieved with a different contact angle between each individual segment electrode wall and the meniscus lens.

In this embodiment, a lens rotation mechanism is provided such that the cylindrical axis of the anamorphic meniscus lens can be automatically and mechanically rotated about the optical axis 45. This enables the variable anamorphic lens to be correctly positioned angularly.

FIG. 7 as described in the previous embodiment illustrates an example of a pattern of applied electrode voltages which may be applied in this embodiment. In this particular embodiment the two pairs of segment electrodes (41 and 43, 42 and 44) of the configuration correspond in angular location to the figure labels 68 and 68', 70 and 70' respectively.

FIG. 6, being a top view cross-section taken perpendicular to the optical axis of the lens, shows a further alternative electrowetting electrode configuration for producing anamorphic lens shapes. This electrode configuration is used to achieve lens shapes with reduced optical aberrations.

As in the previously described alternative electrode configurations of other embodiments of the present invention, the segment electrodes 52 in this embodiment are formed from a conductive material, for example a metal. The inner surface of the enclosure described by the arrangement of electrodes is covered with a continuous, uniform thickness, electrically insulating, fluid contact layer 58 formed for example of Teflon™ AF1600, which constrains the meniscus edge. The segment electrodes 52 are spaced about the optical axis 50 with their longitudinal edges parallel to define an enclosure. In this example, individual segment electrodes 52 are arranged to form a cylindrical enclosure about the optical axis 50. The longitudinal edge of each individual electrode is connected to the parallel and adjacent longitudinal edge of the adjacent electrode by an electrically resistive film 56. It should be appreciated that the film 56 is less conductive than the electrodes 52. The width of each segment electrode 52 along the sidewall is preferably identical and smaller than the distance between two adjacent longitudinal edges of individual segment electrodes connected by the resistive film 56.

Across the width of the resistive film 56 between adjacent electrodes there is a gradual change in voltage between the two applied voltages of the electrodes as opposed to a discrete change. As a result, the contact angle between the fluid meniscus and the fluid contact layer 58 gradually changes along the width of the resistive film 56. The contact angle remains constant across the width of the segment electrodes 52. However, the smaller width of the segment electrodes relative to the distance between the adjacent longitudinal edges of individual segment electrodes connected by the resistive film 56 helps to further reduce discontinuous variation of the contact angle along the edge of the fluid. These factors ensure that optical aberrations of the meniscus lens are reduced.

Now referring to FIGS. 4 and 6 and with the substitution of the configuration of segment electrodes shown in FIG. 4 by this alternative segment electrode configuration, the method of operation is largely similar to that described in the previously described alternative electrode configuration.

Anamorphic meniscus lens shapes can be achieved by combinations of different applied voltages across pairs of opposite segment electrodes and the endwall electrode.

Referring to FIG. 7, as described in the previous two embodiments, the pattern of applied voltages across the segment electrodes may vary with angular spacing about the optical axis 50 as shown therein. The number of electrodes 52 may be any of four or more. Furthermore, the correct angular positioning of the anamorphic meniscus lens about the optical axis 50 can be achieved by rotation about the optical axis 50 of the pattern of applied voltages across the pairs of segment electrodes and the endwall electrode.

Figure 8:
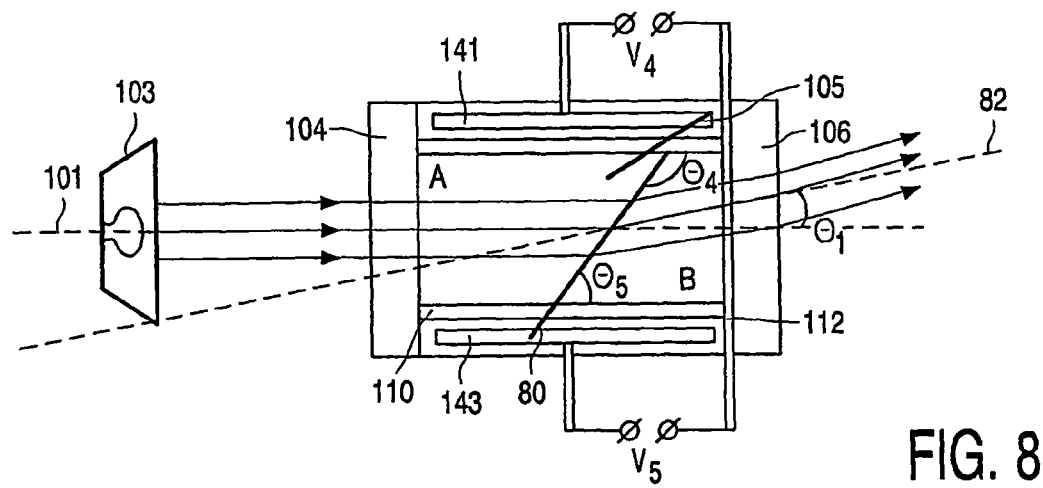
FIGS. 8 to 10 show simplified side view cross-sections of fluid meniscus apparatus suitable for refractive light deflection, in accordance with embodiments of the present invention.

FIG. 8 shows a side view cross-section of a fluid meniscus configuration suitable for refractive light deflection in accordance with an embodiment of the present invention. This embodiment is similar in various respects to previous embodiments and elements similar to that described in relation to FIGS. 1, 2 and 3 are provided in FIG. 8 incremented by 100, and the previous description should be taken to apply here. The sidewall segment electrodes 141 and 143 are similar to the electrodes 41 and 43 as illustrated in FIG. 5 and hence are also incremented by 100. In this embodiment a second pair of sidewall segment electrodes exists (not shown). The electrodes of this second electrode pair are similar to electrodes 42 and 44 of FIG. 5 and are therefore numbered as 142 and 144. This second electrode pair, when viewed cross-sectionally, is positioned perpendicular to the first electrode pair 141 and 143 in a similar arrangement to that of electrode pairs 41, 43 and 42, 44 illustrated in FIG. 5. Previous descriptions of these electrodes should be taken to apply here.

The applied voltage $V_4$ across the endwall electrode 112 and the sidewall electrode 141 results in the fluid contact angle $\theta_4$, for example 60°, between the liquid A and the fluid contact layer 110. Similarly, the applied voltage $V_5$ across the endwall electrode 112 and the sidewall electrode 143 results in the fluid contact angle $\theta_5$. In this embodiment applied voltages $V_4$, $V_5$ are selected such that the sum of the contact angles $\theta_4$ and $\theta_5$ equal 180°. This condition results in a flat fluid meniscus 80 between the liquids A and B when the applied voltages across both sidewall electrodes 142 and 144 with the endwall electrode (herein referenced $V_6$ and $V_7$ respectively) are substantially equal to each other and of an appropriate value such that the fluid contact angles $\theta_6$ and $\theta_7$ are each 90°.

An incoming light beam with a first optical axis 101 from the light source 103 is deflected in one dimension, in a direction perpendicular to the sidewall electrodes 141 and 143, by the flat fluid meniscus 80 to produce an existing light beam with a second optical axis 82. The first optical axis and the second optical axis are related to each other by the deflection angle $\phi_1$. The deflection angle $\phi_1$ can be varied by variation of the applied electrode voltages $V_4$, $V_5$, provided that the sum of the contact angles $\theta_4$ and $\theta_5$ continues to equal 180°.

By swapping the applied voltages $V_4$ and $V_5$ with each other, a negative deflection angle of $\phi_1$ is obtained between the second optical axis 82 from the first optical axis 101 in the same angular plane. By way of example, the smallest possible value of the fluid contact angle $\theta_1$ is approximately 60°. When liquid A is a highly diffractive oil, for example a modified silicone oil, with a refractive index of 1.60 and liquid B is water with a refractive index of 1.33, the maximum value of the deflection angle $\phi_1$ is approximately 9°. This small angle enables precise deflection of the light beam to be obtained. Combined with a negative value of the deflection angle $\phi_1$ of also approximately 9°, the total deflection angle $\phi_T$ (not shown) equals approximately 18° for an incoming beam of light.

Furthermore in this embodiment, further one dimensional deflection of an incoming light beam in a plane perpendicular to that of the deflection angle $\phi_1$ is achieved by controlling the applied voltages $V_6$ and $V_7$ across the endwall electrode 112 and sidewall electrodes 142 or 144 respectively (not shown) such that the sum of the corresponding fluid contact angles $\theta_6$ and $\theta_7$ (not shown) also equals 180°. Values of the applied voltages $V_6$ and $V_7$ are selected to be not equal to each other so that the fluid contact angles $\theta_6$ and $\theta_7$ do not equal 90°. By variation of the applied electrode voltages $V_6$, $V_7$, whilst maintaining that the sum of $\theta_6$ and $\theta_7$ equals 180°, an incoming beam of light with the first optical axis 101 can be deflected by the second deflection angle $\phi_2$ (not shown), lying in a plane perpendicular to the deflection angle $\phi_1$. Again, a negative value of the deflection angle $\phi_2$ in the same angular plane can be achieved by swapping the applied voltages $V_6$ and $V_7$ with each other.

By the selective variation of the two deflection angles $\phi_1$ and $\phi_2$ together the incoming light beam can be deflected in three dimensions, therefore.

As for a previous embodiment, a rotation mechanism is provided such that the electrowetting electrodes may be rotated about the optical axis 101. This enables correct angular positioning of the fluid meniscus to be obtained.

Figure 9:
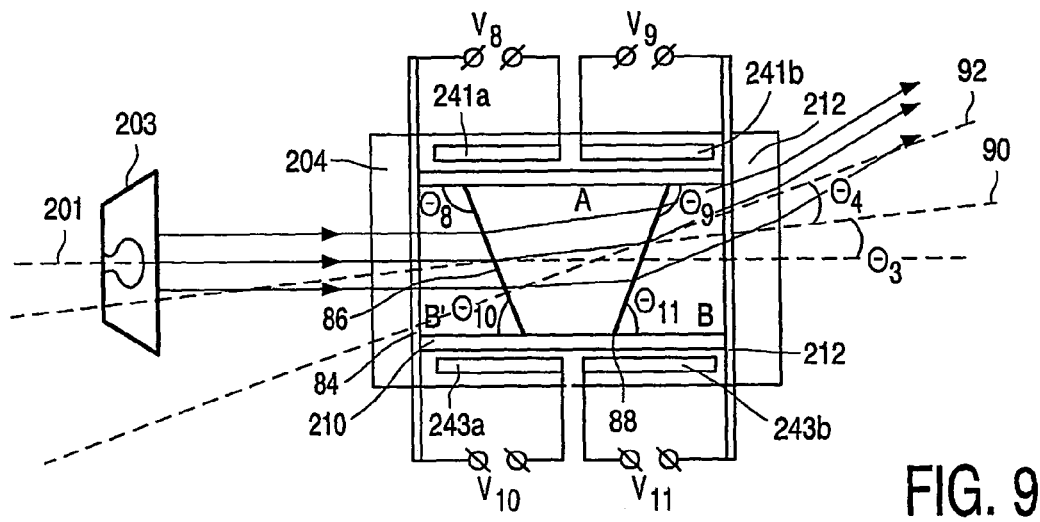

FIG. 9 shows a side view cross-section of fluid meniscus configuration suitable for refractive light deflection in accordance with an embodiment of the present invention. This embodiment of the present invention enables a total deflection angle $\phi_T$ of an incoming light beam of approximately 38° to be achieved, a greater angle of total deflection than the previous embodiment. As for the previous embodiment, elements of this embodiment which are similar to those described in relation to FIGS. 1, 2, 3 and 5 are provided in FIG. 9 incremented by 200, and previous descriptions should be taken to apply here. In this embodiment a second endwall electrode 84 is provided, which is annular in shape and adjacent the front element 204. This second endwall electrode is arranged with at least one part in the fluid chamber such that the electrode acts upon a second fluid layer of liquid B, labeled B' in FIG. 9. The second layer of liquid B (label B') is separated from the layer of liquid A by a first fluid meniscus 86. A second fluid meniscus 88 separates liquid layer A and B. The liquid B' comprises the same liquid as liquid B as described in previous embodiments. It should be noted however that liquid B' may be an alternative fluid which is non-miscible with liquid A, electrically conducting and preferably of a substantially equal density to liquids A and B.

In this embodiment, two axially-spaced sets of electrowetting electrodes are spaced about the perimeter of the sidewall and arranged as shown in FIG. 5. One set includes electrodes 241a, 243a. The other set includes electrodes 241b, 243b. As according to the similar description of previous embodiments, variation of the applied voltages $V_8$ and $V_{10}$ across the second endwall electrode 84 and sidewall electrodes 241 or 243 respectively causes the corresponding fluid contact angles $\theta_8$ and $\theta_{10}$ to vary. The first fluid meniscus 86 is flat when the sum of the fluid contact angles $\theta_8$ and $\theta_{10}$ equals 180°. Similarly, the shape of the second fluid meniscus 88 can be varied by variation of the applied voltages $V_9$ and $V_{11}$ across the first endwall electrode 206 and sidewall electrodes 241 and 243 respectively. The second meniscus 88 is flat when the sum of the fluid contact angles $\theta_9$ and $\theta_{11}$ equals 180° with the applied voltages $V_9$ and $V_{11}$.

An incoming light beam from the light source 203 with a first optical axis 201 is deflected one dimensionally in the plane of sidewall electrodes 241, 243 by the flat first fluid meniscus 86. The deflected light beam has a second optical axis 90 and is angularly related to the first optical axis 201 by a deflection angle $\phi_3$. The deflected light beam with the second optical axis 90 is further deflected by the flat second fluid meniscus 88. The resultant further deflected light beam has a third optical axis 92 which is angularly related to the second optical axis 90 by the deflection angle $\phi_4$. The sum of deflection angles $\phi_3$ and $\phi_4$ gives the combined deflection angle of the incoming light beam by the variable fluid meniscus apparatus. As detailed in previous embodiments, by further applying voltages across each endwall electrode 204, 206 and each sidewall electrode 242, 244 (not shown) respectively, lying perpendicular to sidewall electrodes 241, 243, the flat menisci 86 and 88 can be controlled to deflect an incoming light beam from the light source 203 in a further angular plane perpendicular to that of deflection angles $\phi_3$, $\phi_4$ and hence deflect an incoming light beam in three dimensions. By swapping applied voltages across sidewall electrode pairs with each other a negative value of the deflection angles $\phi_3$, $\phi_4$ can be achieved, as described previously.

Similarly to previous embodiments, the electrowetting electrodes of this embodiment may be rotated about the optical axis 201 either electrically or by using a provided rotation mechanism to achieve correct angular positioning of the fluid meniscus.

In a further envisaged embodiment the two flat fluid menisci 86, 88 are arranged to lie parallel each other, using only a single set of electrodes spaced about the perimeter of the chamber. Such an embodiment may be used in applications including a variable prism similar to that shown and described using FIG. 9 or a beam shifter.

Figure 10:
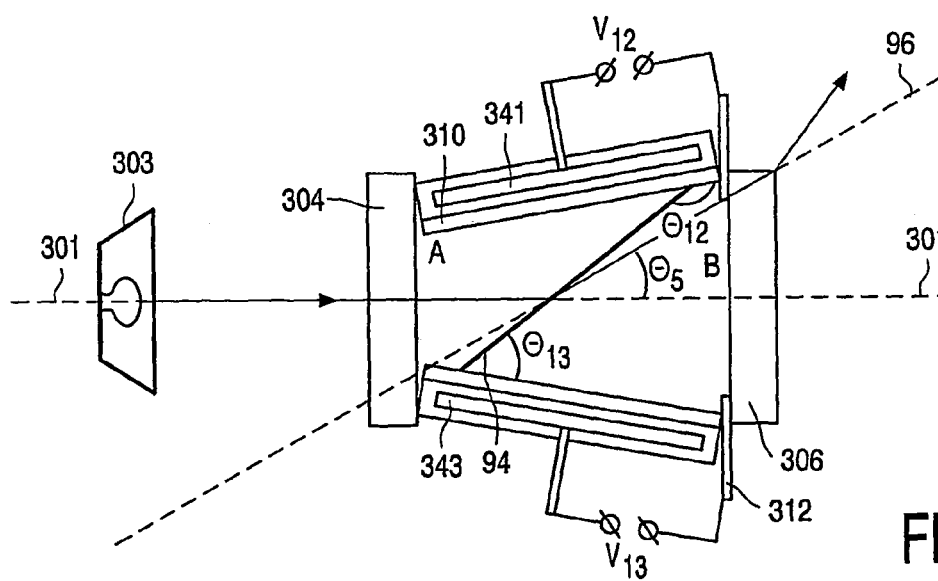

FIG. 10 shows a side view cross-section of a fluid meniscus configuration suitable for refractive light deflection. This embodiment of the present invention enables a greater total deflection angle $\phi_T$ of an incoming light beam of approximately 100° to be achieved than for the previous embodiment.

As for the previous embodiment, elements of this embodiment which are similar to those described in relation to FIGS. 1, 2, 3 and 5 are provided in FIG. 10 incremented by 300, and previous descriptions should be taken to apply here. In this embodiment, the pair of sidewall electrodes 341, 343 do not lie parallel each other. The same applies to the perpendicular pair of sidewall electrodes 342, 344 (not shown). In this embodiment, the sidewall electrodes are arranged as a frustrum.

As according to the similar description of previous embodiments, variation of the applied voltages $V_{12}$, $V_{13}$ across the endwall electrode 312 and the sidewall electrodes 341 or 343 respectively causes the corresponding fluid contact angles $\theta_{12}$ and $\theta_{13}$ to vary. When the fluid contact angles $\theta_{12}$ and $\theta_{13}$ are of appropriate values a flat fluid meniscus 94 is obtained between liquids A and B. As for previous embodiments, an incoming light beam with a first optical axis 301 from the light source 303 is deflected one dimensionally by the meniscus 94 to a direction with a second optical axis 96. The first and second optical axes are related to each other by the deflection angle $\phi_5$. A negative value of the deflection angle $\phi_5$ can be obtained by swapping the applied voltages $V_{12}$ and $V_{13}$ with each other. Similar three dimensional deflection of the light beam as that of previous embodiments can be achieved by variation of the applied voltages across sidewall electrodes 342 or 344 (not shown and perpendicular to sidewall electrode pair 341 and 343) and the endwall electrode 312. Similarly, rotation about the optical axis 301 of the electrowetting electrodes can be achieved by a suitable electrical or mechanical rotation function.

Figure 11:
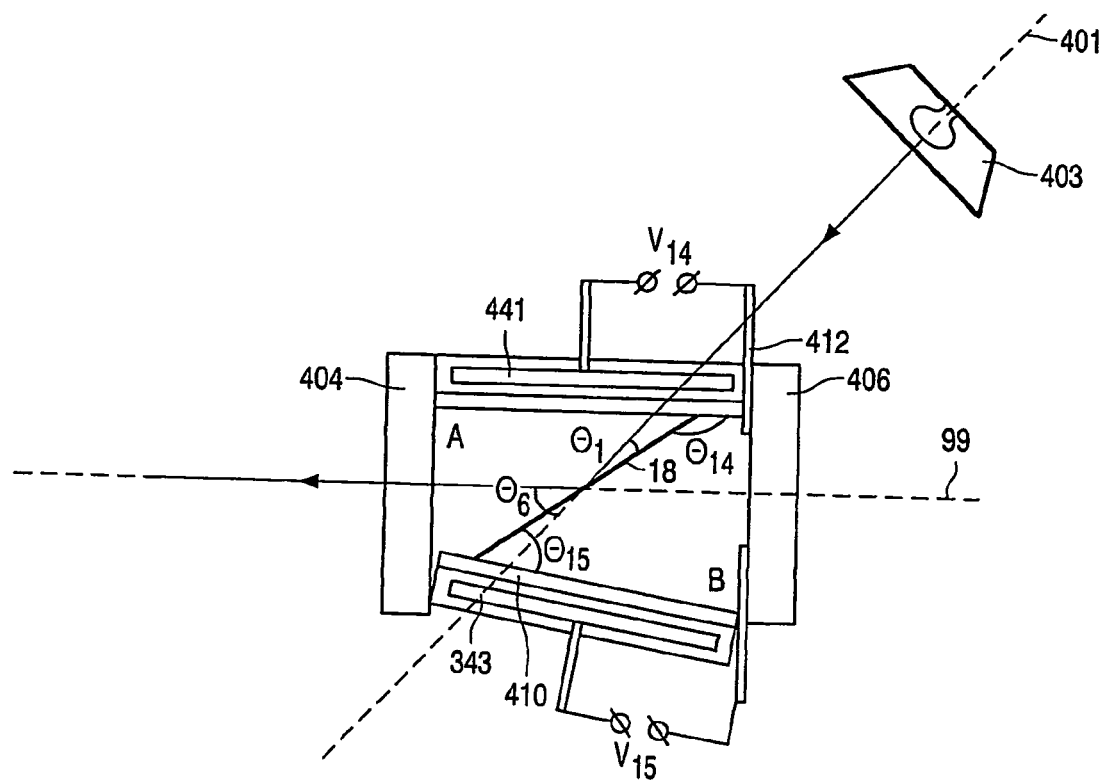
FIG. 11 shows a simplified side view cross-section of fluid meniscus apparatus suitable for reflective light deflection, in accordance with the present invention.

FIG. 11 shows a simplified side view cross-section of a fluid meniscus configuration suitable for a reflective light deflection. In other words the fluid meniscus functions as a mirror. A maximum total angle of deflection $\phi_T$ of an incoming beam of light is approximately 125°. As for previous embodiments, elements of this embodiment which are similar to those described in relation to FIGS. 1, 2, 3 and 5 are provided in FIG. 11 incremented by 400, and previous descriptions should be taken to apply here. In this embodiment, the sidewall electrodes 441, 443 and 442, 444 (not shown) have edges which do not lie parallel each other. It is envisaged as an alternative that the sidewall electrodes may have edges which do lie parallel each other. It is further envisaged that the electrodes whilst having edges lying parallel each other, can be arranged in a triangular configuration. In this embodiment the sidewall electrodes are formed of a material as of previous descriptions with the exception that the material is transparent. Additionally, the fluid contact layer 410 is transparent also.

In a similar manner to previous embodiments the applied voltages $V_{14}$ and $V_{15}$ are applied across the sidewall electrodes 441 or 443 respectively and the endwall electrode 406. Variation of these applied voltages $V_{14}$ and $V_{15}$ results in the corresponding fluid contact angles $\theta_{14}$ and $\theta_{15}$ respectively. With appropriate values of applied voltages $V_{14}$ and $V_{15}$ and therefore the fluid contact angles $\theta_{14}$, $\theta_{15}$ the fluid meniscus 98 between liquids A and B is flat in shape. An incoming light beam with a first optical axis 401 from a light source 403 passes through a transparent sidewall electrode (shown as sidewall electrode 441 in FIG. 11) and strikes the meniscus 98 at an approach angle $\psi_1$. Alternatively, the incoming light beam may pass through a space between adjacent edges of two sidewall electrodes rather than through the sidewall electrode itself. The approach angle $\psi_1$ is below a critical angle value and the incoming light beam is reflectively deflected by the meniscus 98 to follow a second optical axis 99. The first optical axis 401 and the second optical axis 99 are related by the deflection angle $\phi_6$. Providing that the approach angle $\psi_1$ is below the critical value, the deflection angle $\phi_6$ can be varied one dimensionally by variation of applied voltages $V_{14}$, $V_{15}$ and therefore fluid contact angles $\theta_{14}$, $\theta_{15}$ whilst ensuring that the meniscus 98 remains flat. Three dimensional reflection of the incoming light beam can be achieved by further applying voltages across the endwall electrode 406 and the sidewall electrode 442 or 444 (not shown). The applied voltages need to be of appropriate values to ensure a flat meniscus. Reflection of the incoming light beam in an angular plane perpendicular to that of the deflection angle $\phi_6$ occurs when the second approach angle $\psi_2$ (not shown) of the incoming light beam striking the meniscus 98 is below a critical angle. Three dimensional deflection of the incoming light beam is achieved by a combination of both the deflection angles. As for previous embodiments the electrowetting electrodes can be rotated by a rotation mechanism about the second optical axis 99 to achieve correct angular positioning of the meniscus.

Figure 12:
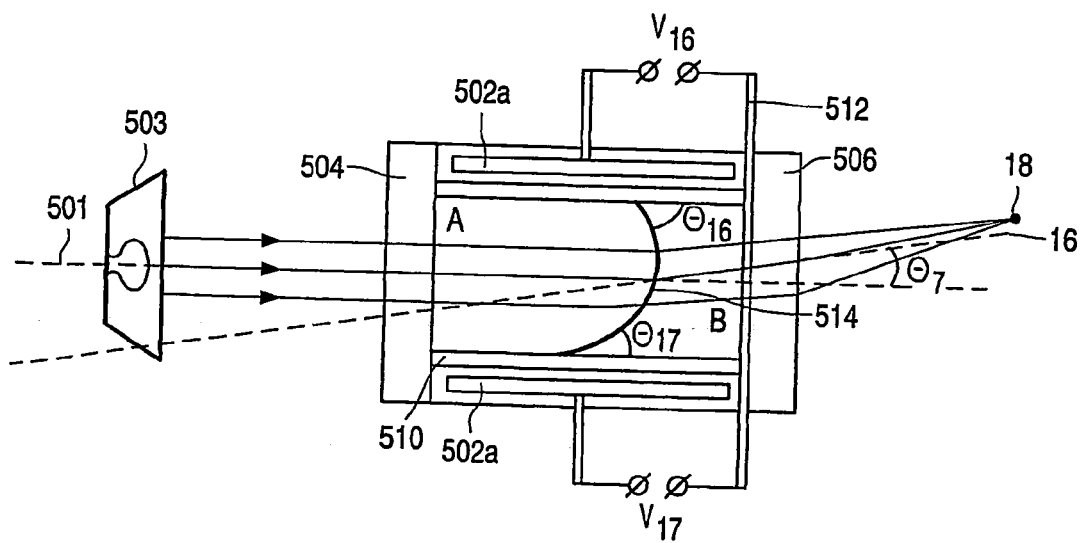
FIG. 12 shows a cross-section side view of fluid meniscus apparatus capable of deflecting and focusing a light beam in accordance with an embodiment of the present invention.

FIG. 12 shows an embodiment of the present invention in a side view cross-section suitable for deflection and focusing of light beams.

This embodiment is similar in various respects to previous embodiments and elements similar to that described in relation to FIGS. 1, 2, 3 and 4 are provided in FIG. 12 incremented by 500, and the previous descriptions should be taken to apply here.

As detailed in previous embodiments, applying a voltage $V_{16}$, $V_{17}$ across the endwall electrode 512, and the sidewall electrode 502a or 502a', respectively the corresponding fluid contact angles result, $\theta_{16}$, $\theta_{17}$. The fluid meniscus 514 between liquids A and B adopts a spherical or spherocylindrical shape when the sum of the fluid contact angles $\theta_{16}$, $\theta_{17}$ does not equal 180°. With variation of the applied voltages $V_{16}$, $V_{17}$ and correspondingly therefore the fluid contact angles $\theta_{16}$, $\theta_{17}$ the curvature of the meniscus 514 and also the tilt of the curvature can be varied. An incoming light beam with a first optical axis 501 from the light source 503 is deflected by the meniscus 514 to follow a second optical axis 16. The first optical axis 501 and the second optical axis are related by the deflection angle $\phi_7$. The deflection angle $\phi_7$ can take a value up to approximately 62.5° when the sidewall electrodes 502a, 502a' do not lie parallel each other. When the sidewall electrodes 502a, 502a' are parallel each other a maximum deflection angle $\phi_7$ of approximately 9° results. Further incoming light beams from the light source 503 having parallel optical axes with the first optical axis 501 are deflected by the meniscus by different deflection angles at different points on the meniscus 514 so as to converge at a focal point 18. Variation of the applied voltages $V_{16}$, $V_{17}$ results in one dimensional angular variation of the deflection angles of the incoming light beams and also the position of the focal point 18 in the plane of the sidewall electrode pair 502. By swapping the applied voltages $V_{16}$ and $V_{17}$ with each other, a negative deflection angle of $\phi_7$ is obtained between the second optical axis 82 from the first optical axis 101 in the same angular plane.

Three dimensional deflection of the incoming light beam can be achieved by similar variation of applied voltages across the endwall electrode 512 and further pairs of sidewall segment electrodes for example those similar to the sidewall segment electrodes labeled 2b, 2b' in FIG. 4. Variation of the applied voltages results in similar variation of the curvature of the meniscus 514 and therefore variation of both the deflection angles and the focal point 18 of the light beams.

It should be noted that the deflection of light beams in this embodiment is of a refractive nature, but that reflective deflection is also envisaged.

The switching velocity of the variation of the meniscus configuration and therefore the deflection properties of the meniscus 514 as a consequence of the variation of applied electrode voltages $V_{16}$, $V_{17}$ depends on the viscosity of both liquids A and B, the size of the fluid chamber 5 and the extent of change of the meniscus curvature.

In this example, where the diameter of the cylindrical fluid chamber 5 is 2 mm, the switching velocity is in the range of 10 ms. The diameter of the cylindrical fluid chamber 5 can be of dimensions ranging from a few centimeters to a few micrometers.

Figure 13:
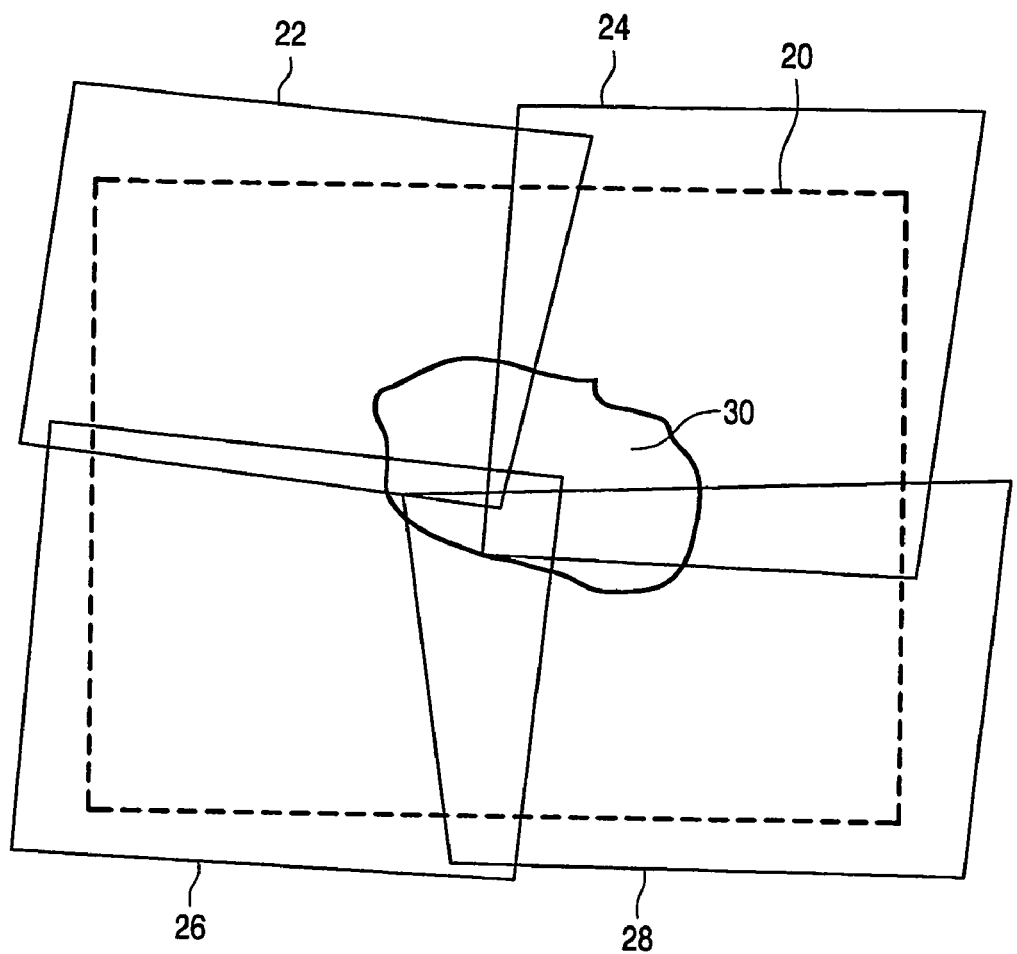
FIG. 13 shows a captured image scene constructed using a mosaicing method in accordance with an embodiment of the invention.

One application of this embodiment of the present invention is in high resolution digital imaging. It is also envisaged that this application can be achieved with the use of the alternative embodiments of the present invention described earlier using FIG. 5 and FIG. 8 or 10 in combination with a solid optical lens. Current methods include the use of expensive imaging sensors with a greater quantity of pixels to obtain a higher resolution image of a target image scene. In a mosaicing method of the present invention, the sensor operates a plurality of times to capture the high resolution image of the target image scene 20, as shown in FIG. 13. With the appropriate incorporation of this embodiment of the present invention in a sensor, for example a camera, the target image scene is recorded by division into several regions. In this example the image scene 20 is divided into four consecutive regions 22, 24, 26, 28 according to a mosaicing pattern. A digital image of each region is recorded individually and consecutively by the camera initially zooming in and focusing on each region prior to capturing the region image. This zooming in and focusing is achieved by variation of the configuration of the fluid meniscus by the variation of applied voltages across electrowetting electrodes as detailed in this embodiment. The rapid ability to change the curvature of the meniscus and therefore the rapidity of which the camera can differently zoom in and focus upon a further region of the target image scene enables a more efficient and higher resolution overall image to be recorded. To achieve this the individually recorded images of the regions of the image scene 22, 24, 26, 28 are positionally mapped relative to each other to construct the recorded image of the target image scene in full. In the instance that the individually recorded target region images 22, 24, 26, 28 do not correctly align with each other perfectly, corrective warping techniques can be applied, for example a polynominal technique. Aligning and seaming of individual target region images with each other can also be achieved using the identification of a feature 30 of the target image scene 20 within the individual recorded image regions. An example of such a simple seam function based on correlation is an averaging filter. For higher quality seaming the use of wavelet or other multiscale techniques may be used. When the image recording is a moving video the estimation of the motion of image scene features can be used to identify similar features of the target image scene and thus provide a seaming function.

Figure 14:
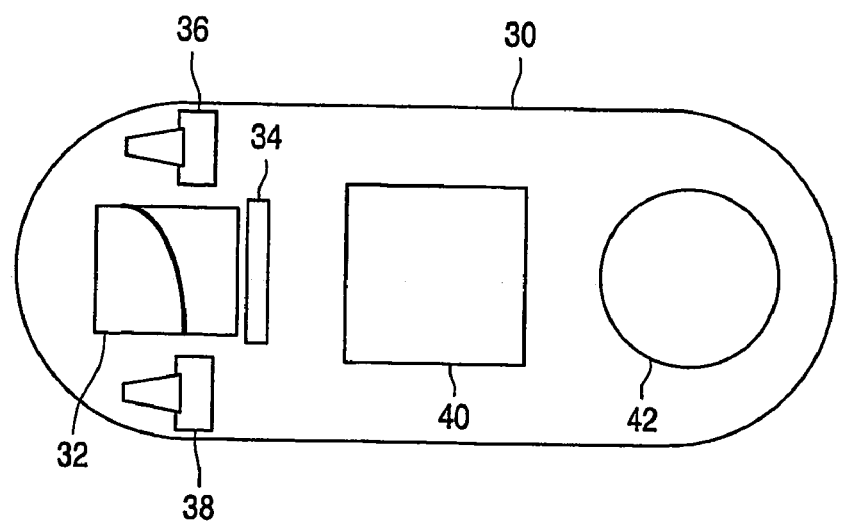
FIG. 14 shows a schematic cross section of a capsule camera arranged in accordance with an embodiment of the invention.

FIG. 14 shows a schematic cross section of a capsule camera arranged in accordance with a further embodiment of the invention. The capsule camera is adapted for in vivo imaging within a patient's body after ingestion thereof, taking image scenes of for example the gastrointestinal tract. The capsule has a waterproof, transparent outer housing 30, of dimensions less than 5 cm by 3 cm such that the capsule may be readily ingested by the patient. A fluid meniscus lens 32, according to any of the embodiments described above, is located inside the capsule housing 30 in front of an imaging sensor 34, for example a Charge Coupled Device (CCD) or Complementary Metal-Oxide Semiconductor (CMOS) image sensor, to provide a variable focus and/or variable deflection of the imaging scene onto the sensor. Two light sources 36, 38, for example Light Emitting Diodes (LEDs), are located adjacent the lens 32, to project light onto the surrounding imaging region. The capsule further includes a control unit 40, which includes image storage memory an/or image transmission apparatus such as a microwave transmitter which transmits images to an external pickup device, and a power source 42, such as a battery or a magnetic coil set which can be externally driven with a magnetic signal to produce electrical power. By use of a variable focus and/or variable deflection fluid meniscus lens 32, arranged in accordance with one of the above-described embodiments, the capsule is provided with a continuously variable focus and/or variable directional imaging function in a compact, low power consumption and lightweight module. Lens 32 may be a single or dual meniscus zoom lens. In the case of a dual meniscus lens two menisci are arranged along the same optical axis to facilitate the implementation of the zoom functionality.

Applications of embodiments of the present invention are relevant to other arrangements of apparatus involving the deflection of light beams. One such example is in the use of bar code scanners which involve reflection of a laser beam on a rotating mirror. The present invention provides benefits including the maximizing of the intensity of the laser spot focused on the bar code being read and hence the sensitivity of the scanner. Additionally the size of the scanner can be reduced.

A further application regards a three-dimensional laser scanner incorporating a focusable liquid lens. Scanning is performed by moving the substrate being scanned relative to the liquid lens. The present invention would allow more efficient scanning to be achieved by variation of the meniscus liquid lens to scan a non-moved substrate.

A yet further application involves the focusing and aiming of the light beams of a vehicle headlamp on a road feature. For example, the headlamps may track a bend in the road to provide the driver with a better view of the road.

Another application is in providing new lighting possibilities for luminaires. An array of light beams for example from an LED can be individually deflected (both focused and aimed) by the present invention to create a plurality of special lighting effects. An alternative application to an array of light beams may involve the deflective fluid menisci incorporated in a window being arranged in parallel to provide a visually clear window, but on switching the deflective menisci to random or curved configurations the window would diffuse incoming light or only allow light to pass through the window in a certain direction.

An imaging application of the present invention involves the incorporation of the variable fluid meniscus in a 'steady-shot' automatic camera or binocular apparatus. Such a device would be able to track and maintain the field of view at a selected part of a scene being imaged by means of a controlled variation of the meniscus configuration. This controlled variation would be influenced by a motion sensor, comprising a set of accelerometers, detecting the motion of the camera relative to the image scene. The device would only require a single electrically controllable element. In a fiber optic application the present invention can be used to switch signals from a first fiber to a second fiber in an array of fibers by controlled variation of the meniscus configuration.

The above embodiments are to be understood as illustrative examples of the invention. Further embodiments of the invention are envisaged.

As a further envisaged embodiment of the present invention, the use of fluid bodies is not limited to the fluids each comprising a liquid. It is possible that one of the fluids may alternatively comprise a gas.

Note that in all embodiments of the present invention a voltage can be applied across individual segment electrodes, rather than pairs of segment electrodes and the endwall electrode. In doing so, independent and different applied voltages may be applied to each of the individual segment electrodes resulting in the formation of more complex meniscus lens shapes. This includes flat meniscus shapes, of which both the directional and rotational orientation can be controlled electrically.

Although the fluid A has a higher refractive index than fluid B in the above examples, the fluid A may also have a lower refractive index than fluid B. For example, the fluid A may be a (per)fluorinated oil, which has a lower refractive index than water. In this case the amorphous fluoropolymer layer is preferably not used, because it might dissolve in fluorinated oils. An alternative fluid contact layer is e.g. a paraffin coating.

Another variation, capable of being applied in relation to the above embodiments, involves the alternative refractive light deflection of an incoming light beam for a described embodiment where reflective light deflection is described, and vice versa.

It is envisaged further that in embodiments of the present invention, further light deflection (refractive or reflective) of an incoming light beam is performed by the transparent electrodes of the apparatus. Appropriate material selection for the forming of these electrodes may depend on the light deflection properties of the material.

It is to be understood that any feature described in relation to any one embodiment may be used alone, or in combination with other features described, and may also be used in combination with one or more features of any other of the embodiments, or any combination of any other of the embodiments.

Furthermore, equivalents and modifications not described above may also be employed without departing from the scope of the invention, which is defined in the accompanying claims.

The invention claimed is:

1. Apparatus for providing a fluid meniscus with variable configurations by electrowetting, the apparatus comprising:
   a fluid chamber;
   two different fluids separated by a meniscus of which an edge, having different sides, is constrained by the fluid chamber;
   a first electrowetting electrode and a second electrowetting electrode, the first electrowetting electrode being arranged to act on a first side of the meniscus edge and the second electrowetting electrode arranged to act separately on a second side of the meniscus edge; and
   a voltage control system for providing a different voltage to said first and second electrowetting electrodes respectively to form a selected meniscus configuration.

2. Apparatus according to claim 1, wherein said fluid chamber includes a fluid contact sidewall arrangement defining a perimeter of the fluid chamber said first and second electrowetting electrodes being mutually spaced about said perimeter.

3. Apparatus according to claim 2, comprising one or more pairs of oppositely lying electrowetting electrodes arranged about said perimeter.

4. Apparatus according to claim 3, comprising two pairs of oppositely lying electrowetting electrodes, the pairs being arranged substantially perpendicular to each other about said perimeter.

5. Apparatus according to claim 2, wherein the electrowetting electrodes are arranged substantially circularly about said perimeter.

6. Apparatus according to claim 2, wherein the width of each electrowetting electrode is smaller than the distance between two adjacent electrowetting electrodes, each being measured in angular distance about the fluid contact sidewall.

7. Apparatus according to claim 2, wherein the width of each electrowetting electrode is larger than the distance between two adjacent electrowetting electrodes, each being measured in angular distance about the fluid contact sidewall.

8. Apparatus according to claim 1, wherein adjacent electrowetting electrodes are connected by an electrically resistive material capable of providing a gradually varying voltage change across the adjacent electrodes.

9. Apparatus according to claim 1, wherein said voltage control system is adapted to be capable of rotating a pattern of voltages about the electrowetting electrodes.

10. Apparatus according to claim 1, comprising a mechanical system for physically rotating the electrowetting electrodes about a rotation axis.

11. Apparatus according to claim 1, further comprising a radiation source for emitting a radiation beam along an optical axis.

12. Apparatus according to claim 1, wherein said voltage control system is adapted to be capable of applying voltages across the electrowetting electrodes so as to provide varying amounts of deflection of an incoming radiation beam by the fluid meniscus, the deflection involving a change of alignment of the optical axis of the radiation beam.

13. Apparatus according to claim 12, wherein the apparatus is configured such that the deflection by the fluid meniscus is of a refractive nature.

14. Apparatus according to claim 12, wherein the apparatus is configured such that the deflection by the fluid meniscus is of a reflective nature.

15. Apparatus according to claim 1, wherein the apparatus is adapted to provide a fluid meniscus configuration in which a first contact angle of the fluid meniscus at the first side is less than 90° and a second contact angle of the fluid meniscus at the second side is greater than 90°.

16. Apparatus according to claim 1, wherein the apparatus is adapted to provide a fluid meniscus configuration in which both a first fluid contact angle of the fluid meniscus at the first side and a second contact angle of the fluid meniscus at the second side of the fluid contact sidewall are less than 90°.

17. Apparatus according to claim 1, wherein apparatus is adapted to provide an anamorphic fluid meniscus configuration.

18. Apparatus according to claim 1, wherein the different fluids within the fluid chamber are of substantially the same density.

19. Apparatus according to claim 1, comprising two or more independently controllable fluid menisci.

20. Medical imaging apparatus including a capsule for use in vivo, said capsule comprising an image sensor for the recording of an in vivo image scene and an apparatus according to claim 1 for providing a fluid meniscus with variable configurations by means of electro-wetting.

21. Medical imaging apparatus according to claim 20, wherein the variable fluid meniscus arrangement is a lens.

22. Medical imaging apparatus according to claim 20, comprising a controller adapted to alter the shape of the variable fluid meniscus of the arrangement to provide at least:
   a first configuration of the variable fluid meniscus for imaging a first in vivo image scene onto said image sensor; and
   a second configuration of the variable fluid meniscus for imaging a different, second in vivo image scene on said image sensor.

* * * * *